US010542882B2

(12) United States Patent
Lichtenauer et al.

(10) Patent No.: US 10,542,882 B2
(45) Date of Patent: Jan. 28, 2020

(54) PHOTOBLEACHING DEVICE AND METHOD AND DARK ADAPTED PERIMETRY DEVICE AND DARK ADAPTED PERIMETRY METHOD

(71) Applicant: MEDMONT INTERNATIONAL PTY LTD, Victoria (AU)

(72) Inventors: Paul Lichtenauer, Victoria (AU); Robert Heavyside, Victoria (AU)

(73) Assignee: Medmont International Pty Ltd., Victoria (AU)

( * ) Notice: Subject to any disclaimer, the term of this patent is extended or adjusted under 35 U.S.C. 154(b) by 0 days.

(21) Appl. No.: 15/526,968

(22) PCT Filed: Nov. 25, 2015

(86) PCT No.: PCT/AU2015/000712
§ 371 (c)(1),
(2) Date: May 15, 2017

(87) PCT Pub. No.: WO2016/081978
PCT Pub. Date: Jun. 2, 2016

(65) Prior Publication Data
US 2017/0325676 A1  Nov. 16, 2017

(30) Foreign Application Priority Data

Nov. 25, 2014 (AU) .................................. 2014904756
Nov. 10, 2015 (AU) .................................. 2015904616

(51) Int. Cl.
*A61B 3/10* (2006.01)
*A61B 3/02* (2006.01)
(Continued)

(52) U.S. Cl.
CPC ............ *A61B 3/024* (2013.01); *A61B 3/0008* (2013.01); *A61B 3/0083* (2013.01)

(58) Field of Classification Search
CPC ... A61B 5/14532; A61B 5/1455; A61B 3/063; A61B 5/6821; A61B 3/10; A61B 3/0008;
(Continued)

(56) References Cited

U.S. PATENT DOCUMENTS 5,325,387 A * 6/1994 Baums ................... G02F 3/026
 372/23
5,598,235 A   1/1997 Heijl et al.
(Continued)

FOREIGN PATENT DOCUMENTS

GB   2500930 A   10/2013
WO   2005023094 A2   3/2005
(Continued)

OTHER PUBLICATIONS

Ernst, W. et al., "An automated static perimeter/adaptometer using light emitting diodes," Jul. 1, 1983, pp. 431-442, vol. 67, No. 7, British Journal of Ophthalmology.
(Continued)

*Primary Examiner* — Brandi N Thomas
(74) *Attorney, Agent, or Firm* — RatnerPrestia

(57) ABSTRACT

A dark adapted perimetry device comprising a photobleaching device, a concave, array guide, the guide comprising a stimulus target array comprising a plurality of stimulus target light sources positioned within the guide and a control unit to selectively illuminate light sources comprised in the plurality of stimulus target light sources at a predetermined luminance is disclosed. The stimulus target light sources may be illuminated by a LED complex source comprising two or more LEDs. Also disclosed is a method using the perimetry device. A bleaching device comprising an eye piece for positioning the eye, a locator for moving the bleaching device into and out of the optical path, an imaging system for tracking the gaze direction or a fixation target, an
(Continued)

illumination source and a bleach control device to control the brightness and pulse form of the illumination source is also disclosed along with a method of photobleaching.

10 Claims, 15 Drawing Sheets

(51) Int. Cl.
*A61B 3/024* (2006.01)
*A61B 3/00* (2006.01)

(58) Field of Classification Search
CPC ......... A61B 3/0083; A61B 3/024; A61B 3/14; A61B 3/0025; A61B 3/066; A61B 3/103; A61B 3/12; A61B 3/06; A61B 3/08
USPC ........ 351/200, 205–206, 209–211, 221, 222, 351/226
See application file for complete search history.

(56) References Cited

U.S. PATENT DOCUMENTS

| | | |
|---|---|---|
| 5,822,037 A | 10/1998 | Barad |
| 7,494,222 B2 | 2/2009 | Jackson et al. |
| 9,050,021 B2 | 6/2015 | Jackson et al. |
| 9,504,379 B2 | 11/2016 | Jackson et al. |
| 9,572,485 B2 | 2/2017 | Jackson et al. |
| 9,730,579 B2 | 8/2017 | Jackson et al. |
| 2011/0007276 A1 | 1/2011 | Jackson et al. |
| 2011/0234977 A1 | 9/2011 | Verdooner |
| 2015/0062530 A1* | 3/2015 | Henry ............ A61B 3/12 351/206 |
| 2015/0201831 A1 | 7/2015 | He et al. |

FOREIGN PATENT DOCUMENTS

| | | |
|---|---|---|
| WO | 2008100613 A2 | 8/2008 |
| WO | 2009055642 A1 | 4/2009 |
| WO | 2012022938 A1 | 2/2012 |
| WO | 2014032337 A1 | 3/2014 |
| WO | 2017035113 A1 | 3/2017 |

OTHER PUBLICATIONS

Extended European Search Report for European Application No. 15 863 161.4, dated Jul. 19, 2018, 8 pages.
International Search Report and Written Opinion for International Application No. PCT/AU2015/000712, dated Jan. 13, 2016—14 Pages.
International Preliminary Report on Patentability for International Application No. PCT/AU2015/000712, dated Mar. 1, 2017—16 Pages.
Dimitrov et al., "Visual function tests as potential biomarkers in age-related macular degeneration"; Investigative Ophthalmoligy Visual Science, 2011, vol. 52, No. 13, pp. 9457-9469).
Dimitrov et al., "Relationship between clinical macular changes and retinal function in age-related macular degeneration"; Investigative Ophthalmology Visual Science, 2012, vol. 53, No. 9, pp. 5213-5220.
Jackson et al., "A short-duration dark adaptation protocol for assessment of age-related maculopathy"; J. Ocul. Biol. Dis. Infor., 2008, vol. 1, pp. 7-11.

* cited by examiner

PHOTOBLEACHING DEVICE AND METHOD AND DARK ADAPTED PERIMETRY DEVICE AND DARK ADAPTED PERIMETRY METHOD

CROSS REFERENCE TO RELATED APPLICATIONS

This application is the National Stage filing of International Appln. No. PCT/AU2015/000712, filed 25 Nov. 2015, and claims priority of AU Application No. 2014904756, filed 25 Nov. 2014, and AU Application No 2015904616, filed 10 Nov. 2015, the entireties of each application are incorporated herein by reference for all purposes.

FIELD OF THE INVENTION

The present invention relates to a photobleaching device and method and a perimetry device and perimetry method. The photobleaching aspects of the present invention provide an even or substantially even bleach over a large field of view. The perimetry device and methods relate to a perimeter comprising a large dynamic range and, optionally, a large field of view.

BACKGROUND TO THE INVENTION

The macula is the central part of the retina responsible for the majority of central vision. It is comprised of the fovea, a small, cone-dominated region, which is surrounded by the rod-dominated parafovea. Photoreceptor density decreases extending out from the macula, with an almost complete loss of cone receptors outside of the inner ten degrees.

Photoreceptors are dependent on the health of the Retinal Pigment Epithelium (RPE) and Bruch's membrane complex. This complex is responsible for nutrient and waste exchange, keeping the photoreceptors healthy and clearing substances such as opsin, which is a by-product of bleaching. As the function of the RPE and Bruch's membrane complex deteriorates, or is otherwise impaired, the photoreceptors suffer from a deficient supply of nutrients and reduced clearing of toxins and by-products of bleaching. This results in a reduction in the health and function of photoreceptors.

Rod photoreceptors are responsible for vision in dim light, while cone receptors allow for responses to bright light and colors. Rods are particularly vulnerable to the effects of reduced function of the RPE and Bruchs membrane complex and as such, this decay results in reduced scotopic, or dark-adapted vision Dark-adaptation can be defined as the recovery of light sensitivity by the retina in the dark after exposure to a bright light (bleaching). As such, dark adaptation provides a useful assessment of the health of the RPE and/or Bruch's membrane complex.

Rod receptors seem to be effected by damage to the RPE and/or Bruch's membrane prior to serious deterioration of cone receptors. This is significant as the early detection of impaired dark adaptation could allow novel treatment options for a range of disease before the serious visual impairment associated with cone defects becomes apparent. As there are no treatment options currently available to reverse damage associated with most retinal diseases, providing treatment before damage is done, is crucial to a successful outcome.

The RPE complex slowly deteriorates with age, but accelerated deterioration is the major cause of early stage AMD. In most eyes, debris that is not cleared through the membrane complex builds up between the Bruch's membrane and the RPE to form drusen. Early or dry AMD progresses to wet AMD when this drusen causes inflammation that sets off a chain reaction resulting in the growth of many small blood vessels up into the RPE. These delicate vessels are prone to bursting, which causes blood to leak into the retina. Both the growth and the leaking blood causes severe damage to the retina and this is the stage of AMD that is most serious. Preventing progression to this stage and treating it when it does occur is the major target for currently marketed pharmaceuticals.

The measurement of dark adaption of the human eye has been known for some time. In more recent years, research has investigated abnormal dark adaption and found a high correlation with the presence of Age-related Macular Degeneration (AMD) and structural changes in the Bruch's membrane. Research has also found that dark adaption anomalies indicate the presence of AMD much earlier than other detectable irregularities.

A study in 2011 found rod recovery to be the best way to detect early AMD but because of the difficulties in measuring rod recovery they ranked it much lower than other techniques (Dimitrov, et al., "Visual function tests as potential biomarkers in age-related macular degeneration"; Invest. Ophthalmol. Vis. Sci., 2011, 9; 52(13):9457-69).

A 2012 study found that dark adaptation showed a strong ability to detect early functional changes that could lead to AMD, but becomes significantly poorer as a monitoring tool after the onset of AMD. Steady state tests such as flicker perimitry (14 Hz flicker) showed a continuous decline as eye function deteriorates and offer a better quality test of disease progression (Dimitrov, et al., "Relationship between clinical macular changes and retinal function in age-related macular degeneration"; Invest. Ophthalmol. Vis. Sci., 2012, 7; 53(9): 5213-20).

The methods known in the prior art involve bleaching the retina of a subject with a bright light source and generating a stimulus with a specific spectrum and intensity to be seen by the subject. When the stimulus is seen the subject acknowledges this. The time delay from the time of bleaching to the time of stimulus and the level of intensity is recorded and further analysed to establish the physiological parameters characteristic for the disease. Multiple measurements of the stimulus point can be taken to increase accuracy of measurement.

A publication by Jackson & Edwards contains a description of a short duration dark adaptation protocol for assessment of age-related maculopathy (ARM) using a Dark Adaptometer called the AdaptDX ("A short-duration dark adaptation protocol for assessment of age-related maculopathy"; J. Ocul. Biol. Dis. Infor., 2008, 1:7-11). The AdaptDX presents a stimulus point at the line of sight. This publication notes that using the twenty minute procedure in combination with the AdaptDx dark adaptometer allows the differentiation of early AMD and normal patients. As the severity of AMD increases, rod recovery rate and rod intercept drop very quickly.

Another known device is based on retinal imaging overlaying the retinal image surface to a projected light pattern. A third apparatus uses a tilting mirror system to produce the stimulus point at desired position.

Improved methods and apparatuses to quickly and efficiently measure dark-adaptation in a patient are highly desirable.

The reference to any prior art in this specification is not, and should not be taken as, an acknowledgement or any form of suggestion that the prior art forms part of the common general knowledge.

OBJECT OF THE INVENTION

It is a preferred object of the embodiments of the present invention to provide an apparatus and method that addresses or at least ameliorates one or more of the aforementioned problems of the prior art and/or provides a useful commercial alternative.

SUMMARY OF THE INVENTION

Generally, separate embodiments of the present invention relate to a photobleaching device, a photobleaching method, a dark adapted perimetry device and a dark adapted perimetry method. The photobleaching aspects of the present invention are of particular advantage because they provide a substantially even illumination at a known quantity of exposure to the retina over a wide or substantially full field of view. Advantageously, the photobleaching aspects of this invention may incorporate a high level of bleaching. Also of significant advantage are the dark adapted perimetry device and dark adapted perimetry methods of the invention which may achieve a large dynamic range and optionally a large field of view.

In a first aspect, although it need not be the only or indeed the broadest form, the present invention provides a bleaching device comprising:
  an eye piece for positioning the eye;
  a locator for moving the bleaching device into and out of the optical path;
  an imaging system for tracking the gaze direction or a fixation target;
  an illumination source; and
  a bleach control device to control the brightness and pulse form of the illumination source.

In a second embodiment, the invention provides a method of photobleaching an eye, the method comprising:
  moving the photobleaching device into an optical path of the eye;
  providing an imaging system for tracking the gaze direction or a fixation target;
  illuminating the eye with an illumination source; and
  controlling the brightness and pulse form of the illumination source with a bleaching control device.

In one embodiment of the first or second aspects, the illumination source comprises a light guide comprising a light guide optical medium and an illumination panel. The illumination panel may comprise a plurality of LEDs. The illumination panel may comprise a circular shape or an unfolded spherical shape. The circular shape may be planar. The unfolded spherical shape may be arcuate. The unfolded spherical shape may comprise a plurality of petals. The illumination panel may be symmetrical. The illumination panel may comprise a flexible printed control board. The plurality of LEDs may comprise a plurality of surface mounted LEDs. The light guide may comprise a reflective or total reflective surface. The light guide may comprise a concave or substantially concave surface. The concave surface may comprise facets. The light guide may comprise a reflective or total reflective surface.

In another embodiment of the first or second aspects, the illumination source comprises an integrating sphere. The integrating sphere may comprise a spherical body comprising a white diffuse coating, a baffle, an entry port and an exit port.

In still another embodiment of the first or second aspects the illumination system comprises any illumination source. The illumination source may comprise a xenon flash or a high intensity LED. The imaging system may comprise an imaging sensor.

In yet another embodiment of the first or second aspects, the bleaching device may comprise a spectral filter to filter the light incident upon the eye. The spectral filter may not cover the imaging system or the fixation target. The spectral filter may comprise an aperture for the imaging system or the fixation target. The spectral filter may be located between an illumination source and a light guide or between a light guide and the eye.

In another embodiment of the first or second aspect, the fixation target is not illuminated and does not provide bleaching to the retina. The fixation target may comprise a dark opaque coating or the lens aperture of a gaze tracking imaging system. The fixation target may be located at the centre of the illumination source. The fixation target may be limited in size to equivalent to the fovea or to about two degrees of visual field.

In another embodiment of the first or second aspect, the bleach control device may comprise a printed circuit board. The printed circuit board may be connected or connectable to a dark adapted perimetry device for sending and receiving communication.

In a third aspect, the invention resides in a dark adapted perimetry device comprising:
  a photobleaching device;
  a concave, array guide the guide comprising a stimulus target array comprising a plurality of stimulus target light sources positioned within the guide; and
  a control unit to selectively illuminate light sources comprised in the plurality of stimulus target light sources at a predetermined luminance.

In a fourth aspect, the invention provides a dark adapted perimetry method comprising:
  at least partially photobleaching an eye;
  selectively illuminating light sources at a predetermined luminance, wherein the light sources are comprised on a concave, array guide, wherein the light sources comprise a stimulus target array positioned within a concave array guide;
  recording response data comprising a triggering of an input device in response to the selective illumination.

In one embodiment of the fourth aspect, the method further comprises applying a normative data set that has been statistically derived though clinical trials to establish normal response characteristics of stimuli. The normative data may be compared with noise reduced response data.

In one embodiment of the third or fourth aspects, only one light source is illuminated at a time. Each time a light source is illuminated it may be illuminated with known exposure parameters for one or more of intensity, spectrum and location relative to a fixation axis. The luminance of a light source may be increased until an input is received. In one particular embodiment, illumination comprises known exposure parameters for all of intensity, spectrum and location relative to a fixation axis In another embodiment of the third or fourth aspects, the dark adapted perimetry device comprises a field of view greater than 40 deg eccentricity. In other embodiments the field of view comprises more than 35; more than 40; more than 50, or more than 70 deg eccentricity. In one particular embodiment the field of view comprises 72 deg eccentricity.

In still another embodiment of the third or fourth aspects, a dynamic range of measurement is about 75 dB. In other embodiments, the dynamic range may be about 50 dB; about 60 dB; about 70 dB; about 80 db; about 90 dB; or about 100 dB.

In yet another embodiment of the third or fourth aspects, the dark adapted perimetry device is able to detect a visual threshold of about $10^{-6}$ cd/m$^2$.

In another embodiment of the third or fourth aspects, each stimulus target light source comprises an optical transmissive element with diffusing light propagation properties, and a circular exit diaphragm which forms the stimulus surface.

In still another embodiment of the third or fourth aspects, each stimulus target light source is connected to a respective optical fibre. Each respective optical fibre may be illuminated by a respective light source. The respective light source may comprise a respective LED complex light source. The LED complex light source may illuminate one or more light guide which illuminates a respective optical fibre.

In another embodiment of the third or fourth aspects, luminance of each stimulus target light source is modulated using one or more of pulse width modulation (PWM), LED current level modulation and multi source modulation of the light source.

In still another embodiment of the third or fourth aspect, the on level of the PWM is the LED current of a first LED within the LED complex source.

In yet another embodiment of the third or fourth aspect, each respective LED complex light source may comprise a high intensity LED and a low intensity LED of the same wavelength to the high intensity LED. The wavelength of the high intensity LED and the low intensity LED may comprise red.

The light power range of the high intensity LED and the low intensity LED may overlap, however the maximum intensity of the high intensity LED is higher than the maximum intensity of the low intensity LED. The maximum intensity of the high intensity LED may ay be 25 dB higher than the low intensity LED.

In another embodiment the LED complex source may further comprise a LED of a second wavelength. The second wavelength LED may comprise green.

In another embodiment of the third or fourth embodiment, the device may further comprise a fixation target, wherein the intensity of the fixation target may be changed with the bleaching recovery of the subject.

The dark adapted perimetry device of the third or fourth aspect may further comprise a shield.

The dark adapted perimetry device of the third or fourth aspect may further comprise a processing unit. The processing unit may correlate neighbouring stimulus signals. The correlation may comprise at least two neighbouring stimulus target light sources. The correlation may comprise a weighting function. The weighting function may be dependent on the distance between the points and the statistical confidence of the data points.

The device of the third aspect or the method of the fourth aspect may be used to detect a visual disease or condition such as AMD.

In one embodiment, the concave array guide may be spherical or substantially spherical.

In one embodiment of the third or fourth aspect, the plurality of light sources display a spectral distribution with a dominant wavelength that coincides with the peak sensitivity of the rod and the cone receptors (L, M and S receptors). In another embodiment only one wavelength is displayed at a time.

In one embodiment of the third or fourth aspect, at least three measurements are performed at three different wavelengths. The three wavelengths may comprise one that is sensitive to scatter (blue); one that is less sensitive to scatter (red); with the third one between these two (yellow or blue (cyan) at the visual axis of the retina. The at least three measurements and different wavelengths may comprise four.

In one embodiment of the third or fourth aspect, the device further comprise an alignment illumination source, wherein the reflection of the alignment illumination source may be used in a captured image of the eye to provide information on the alignment of the eye.

In another embodiment of the third aspect, the photobleaching device may comprise the device of the first aspect.

In another embodiment of the fourth aspect, the photobleaching may comprise the method of the second aspect.

Further aspects and/or features of the present invention will become apparent from the following detailed description.

BRIEF DESCRIPTION OF THE DRAWINGS

In order that the invention may be readily understood and put into practical effect, reference will now be made to embodiments of the present invention with reference to the accompanying drawings, wherein like reference numbers refer to identical elements. The drawings are provided by way of example only, wherein.

Figure 1:
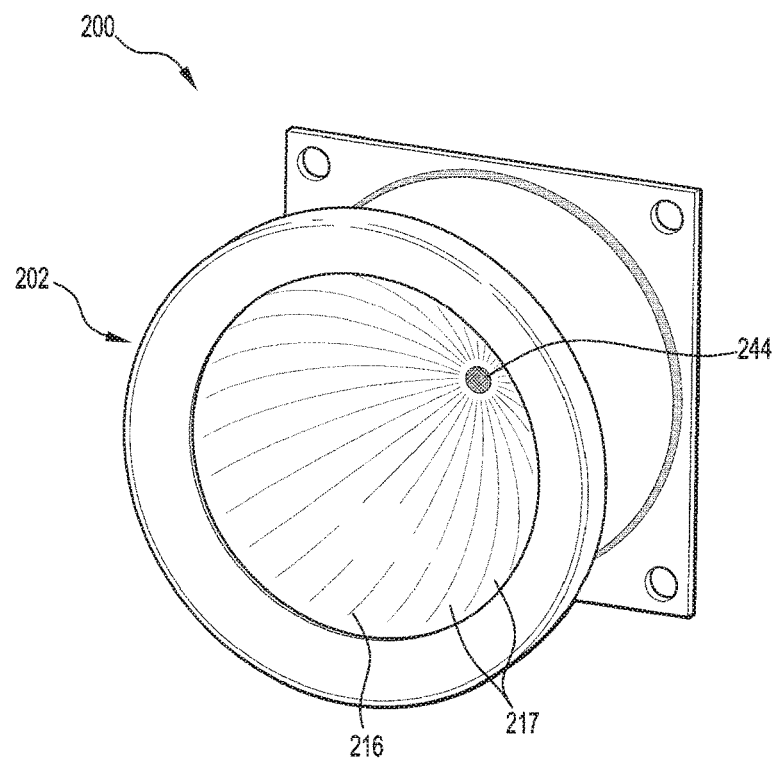
FIG. 1 shows a perspective view of a photobleaching device according to a first embodiment of the invention comprising a fixation target.

Skilled addressees will appreciate that elements in the drawings are illustrated for simplicity and clarity and have not necessarily been drawn to scale. For example, the relative dimensions of some elements in the drawings may be distorted to help improve understanding of embodiments of the present invention.

DETAILED DESCRIPTION OF THE INVENTION

Separate embodiments of the present invention relate to a photobleaching device, a method of photobleaching, a dark adapted perimetry device and a method for dark adapted perimetry. The methods and devices of the present invention may be used to detect a visual disease or condition such as, AMD.

Advantageously, the present invention may allow early retinal disease detection and/or physiological parameter determination of the human eye.
Photobleaching The photobleaching device of the present invention provide improved diagnostic accuracy and resolution, by producing a substantially even illumination at a known quantity of exposure to the retina over a wide or substantially full field of view. Hitherto, this has not been achieved. The present inventors have made this possible by applying a bleach control device within the photobleaching device.

Figure 14:
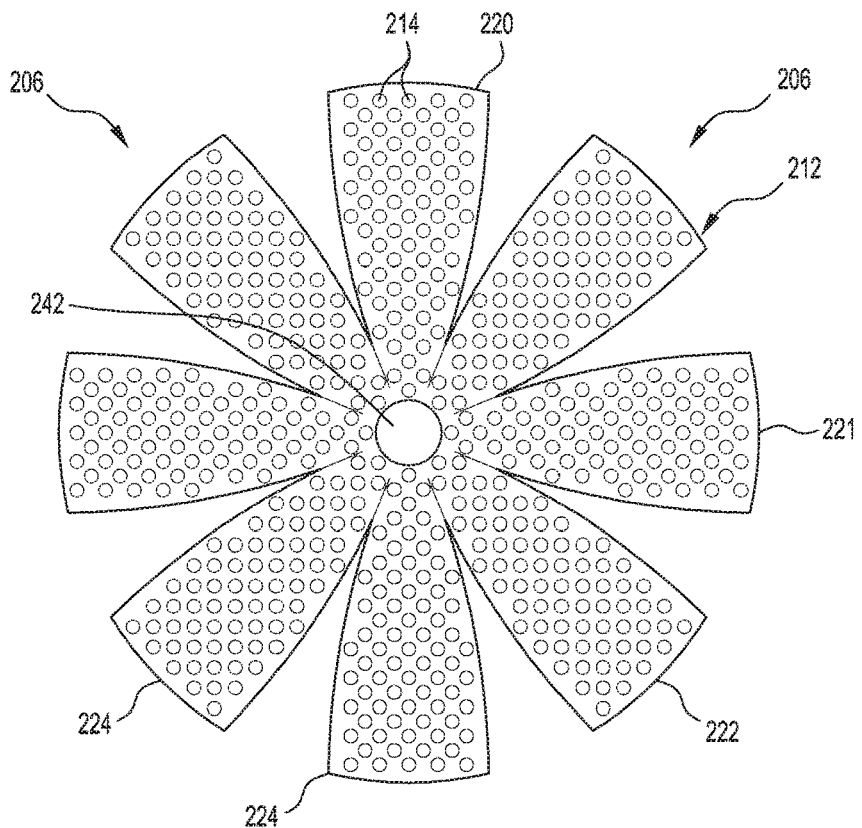
FIG. 14 shows a front view of a curved light source suitable for use in the photobleaching device shown in FIG. 13.
Figure 15:
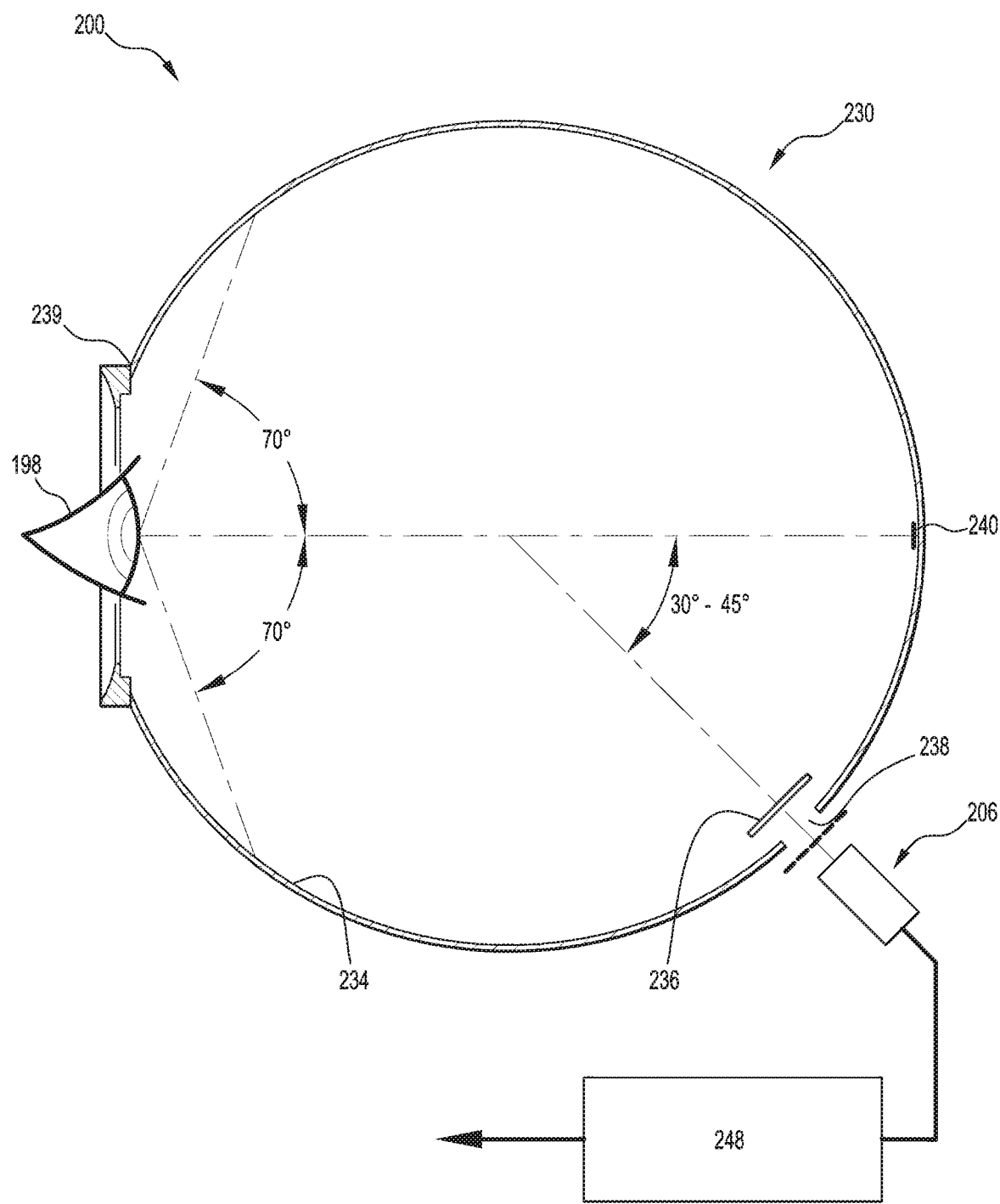
FIG. 15 shows a section view of a photobleaching device according to a third embodiment of the invention comprising a fixation target.
Figure 16:
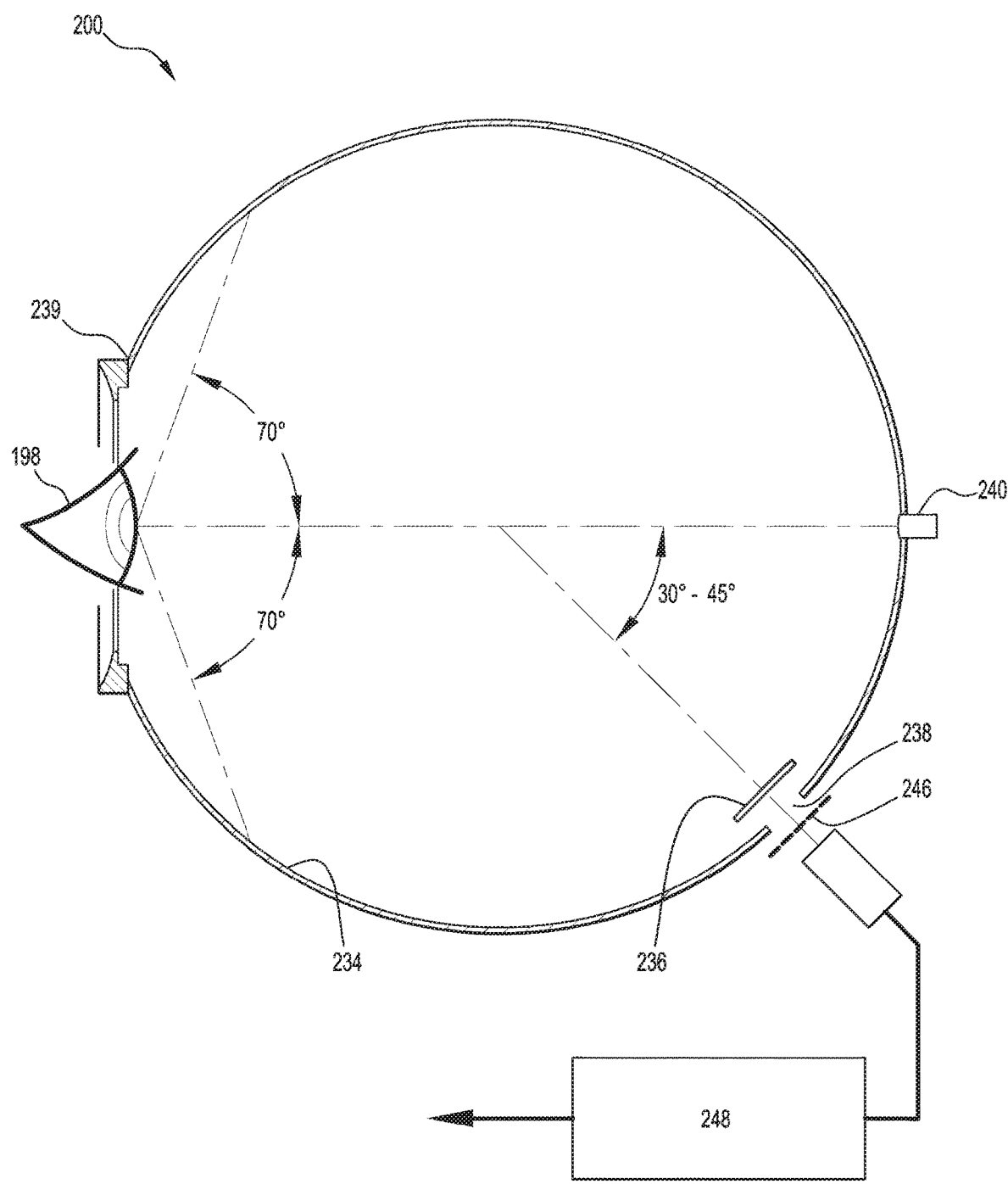
FIG. 16 shows a section view of a photobleaching device according to a third embodiment of the invention comprising an imaging system.
Figure 17:
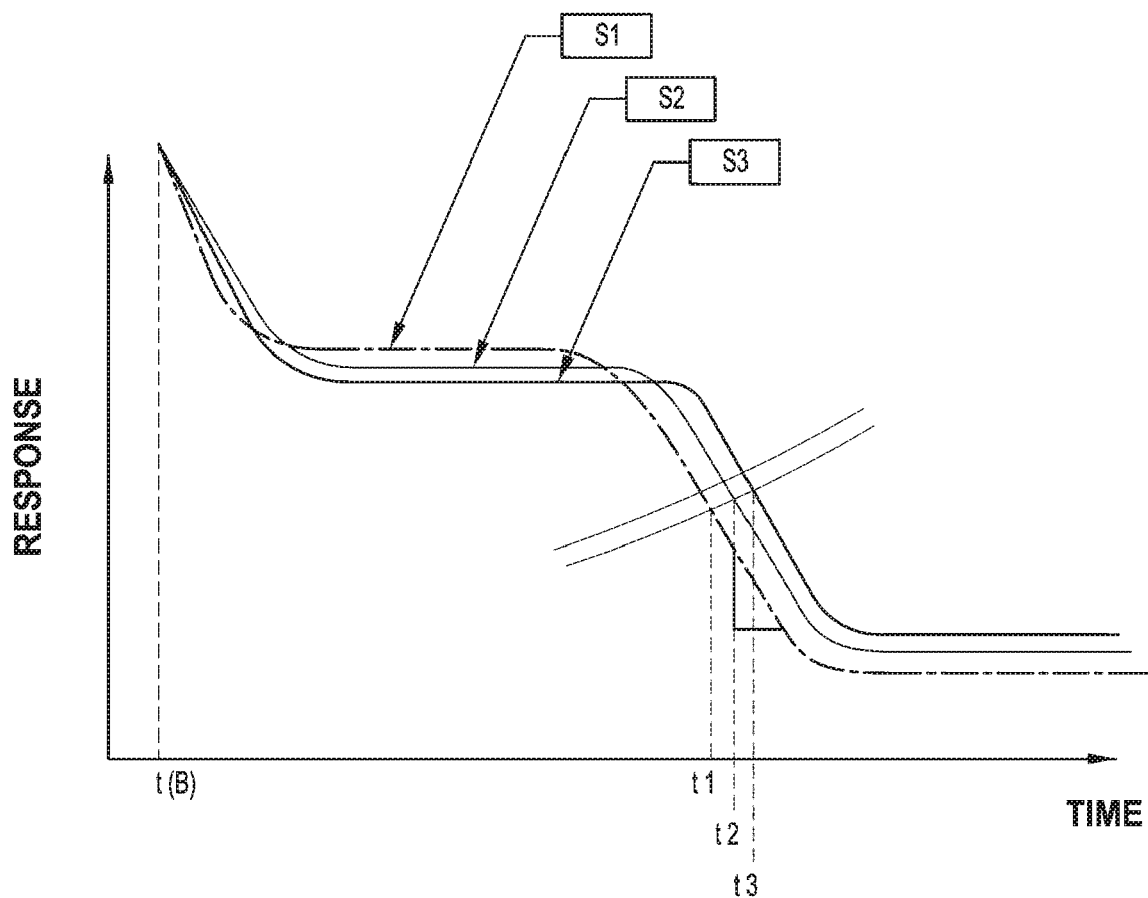
FIG. 17 is a graph showing response data collected using the dark adapted perimetry device of the invention.

FIGS. 1 to 16 show some embodiments of a photobleaching device 200 according to the invention. FIGS. 1 to 10 show a light guide 208 bleaching embodiment. FIGS. 11 to 14 show a light guide 208 bleaching with a curved light source 221 embodiment. FIGS. 15 and 16 show an integrating sphere 230 bleaching embodiment.

Figure 18:
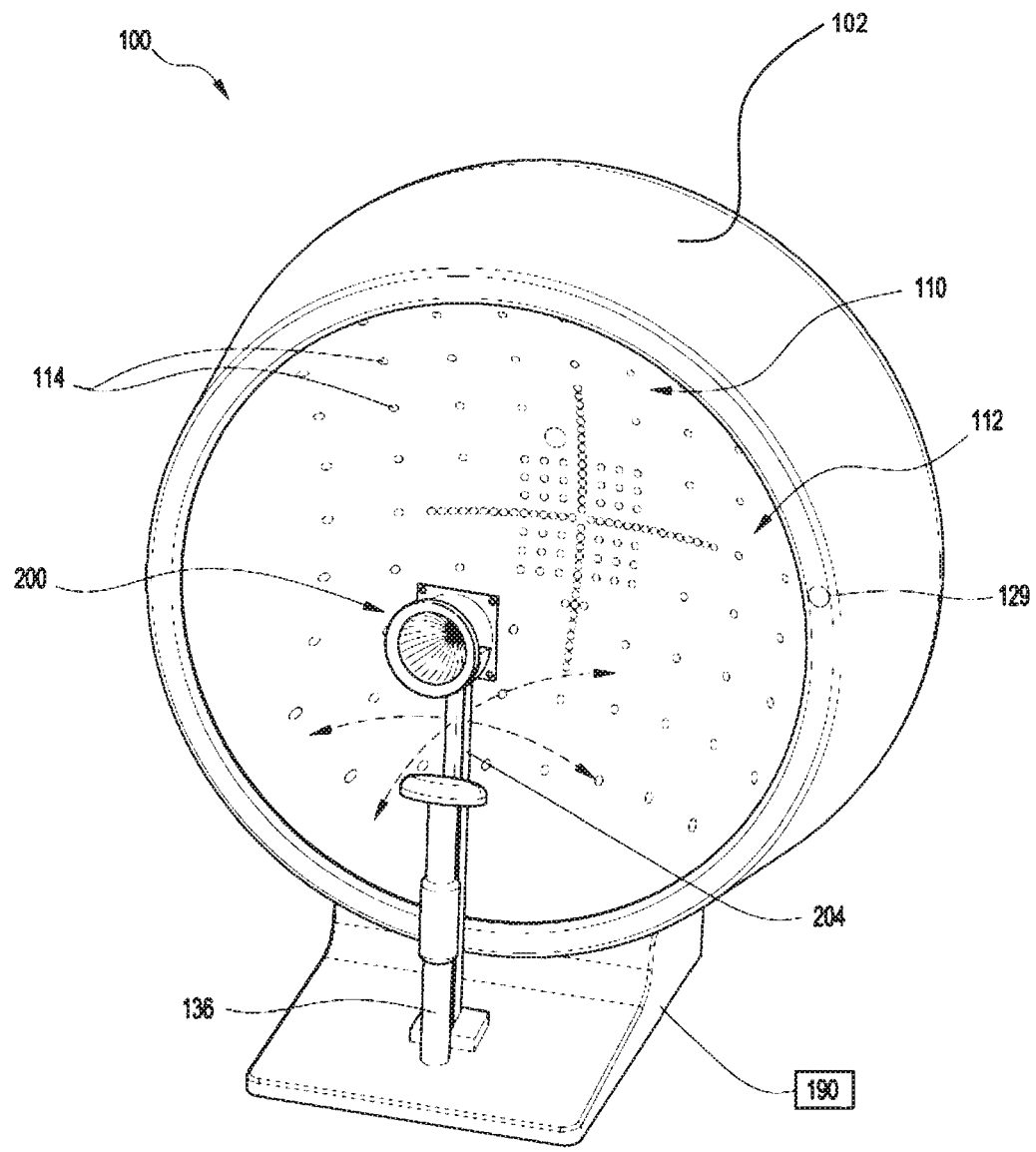
FIG. 18 shows a perspective view of a dark adapted perimetry device according to a first embodiment of the invention.
Figure 19:
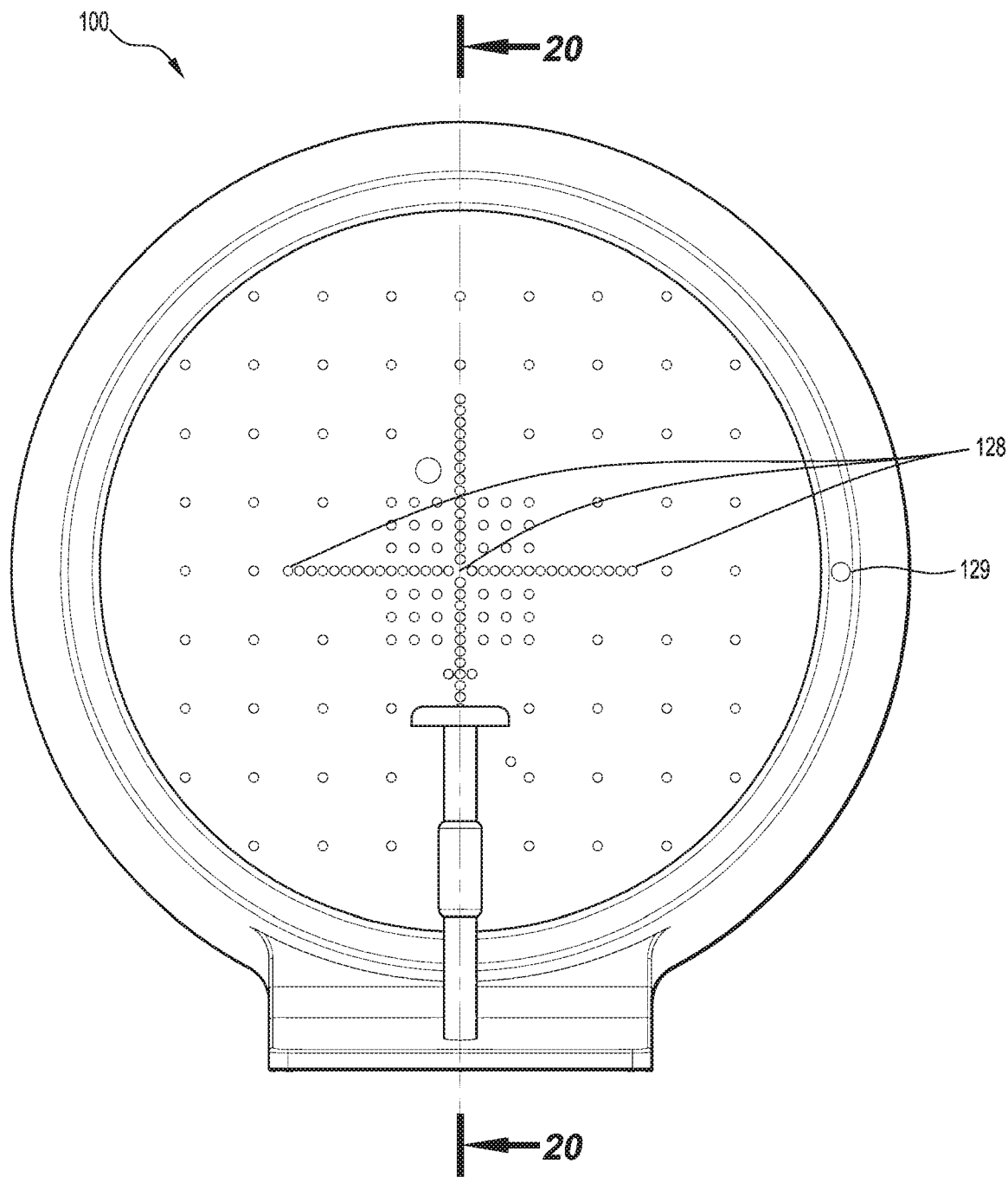
FIG. 19 shows a front view of the dark adapted perimetry device shown in FIG. 18.

Regardless of embodiment, photobleaching device 200 comprises an eye piece 202 for positioning eye 198. As shown in FIG. 18 a locator 204 is provided for moving device 200 into and out of the optical path. The locator 204 may be located on any part of device 200 and may comprise any mechanical or electromechanical means of movement. As shown with arrows in FIG. 18, locator 204 can move in two planes, clockwise and anti-clockwise to rotate into and out of the optical path and proximally and distally with respect to eye 198. Once photobleaching device 200 is in position, eye 198 may be illuminated with illumination source 206.

In the embodiments shown in FIGS. 6 to 10, 13 to 14 and 16 device 200 comprises an imaging system 242 for tracking the gaze direction. Imaging system 242 comprises a lens 241 and an imaging sensor 242.

In the other embodiments, instead of an imaging system 242, device 200 comprises a fixation target 244 which may comprise a black opaque coating that is not illuminated. The fixation target does not provide bleaching to the retina. In another embodiment the fixation target 244 may comprise a lens aperture of a gaze tracking device 122. The fixation target 244 may be located at the centre of the illumination source 206. The fixation target 244 may be limited in size to be equivalent to the fovea or to about two degrees of visual field. Advantageously, the retinal fixation area focused on fixation target 244 remains unexposed or partially unexposed during bleaching, which means the unbleached photoreceptors may respond to low level illumination and identify the fixation target 244, while the bleached receptors remain unresponsive to the low level illumination.

Figure 2:
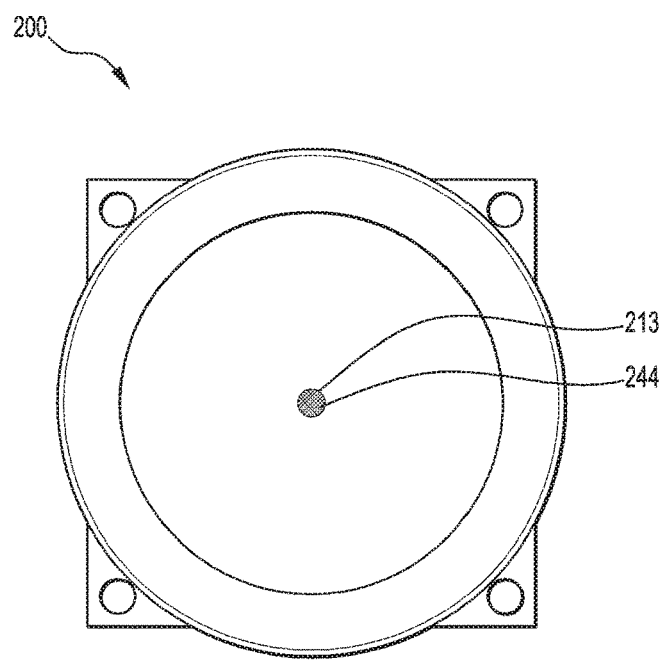
FIG. 2 shows a front view of the photobleaching device shown in FIG. 1.
Figure 3:
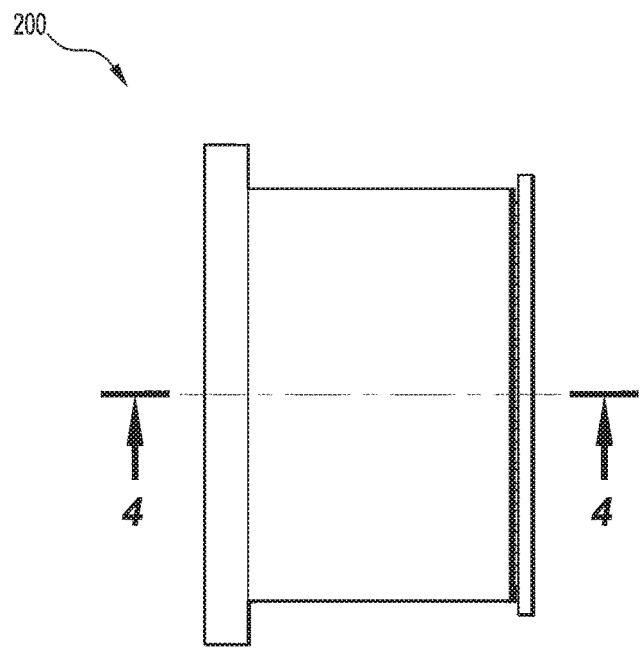
FIG. 3 shows a side view of the photobleaching device shown in FIG. 1.

Each of the light guide 208 bleaching embodiments (FIGS. 1 to 10); light guide 208 bleaching with a curved light source 221 embodiment (FIGS. 11 to 14) and integrating sphere 230 bleaching embodiments (FIGS. 15 and 16) also comprise an illumination source 206. The light guide 208 bleaching embodiments and light guide 208 bleaching with a curved light source 221 embodiments are shown to comprise a light guide 208, while FIG. 2C shows an embodiment comprising an integrating sphere 230.

Figure 6:
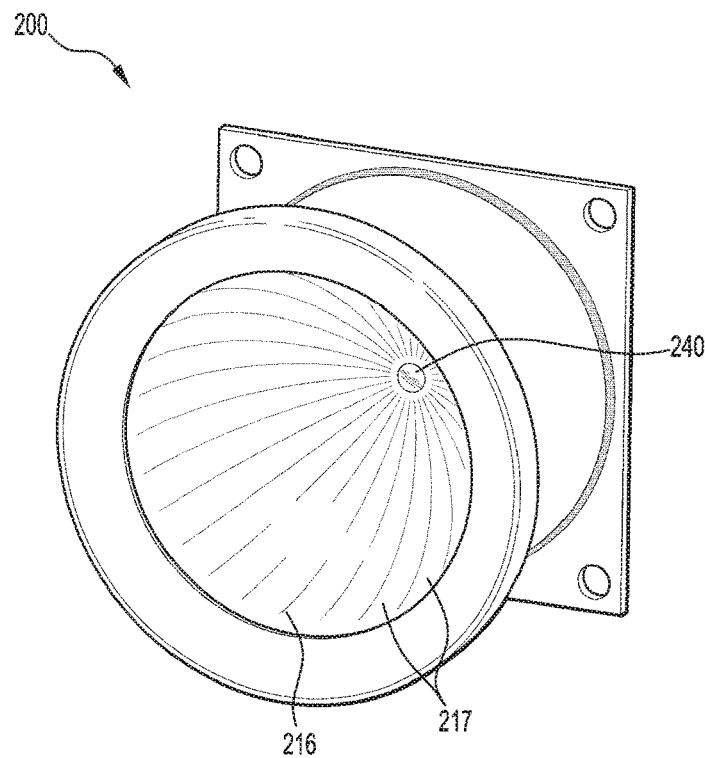
FIG. 6 shows a perspective view of a photobleaching device according to a first embodiment of the invention comprising an imaging system.
Figure 7:
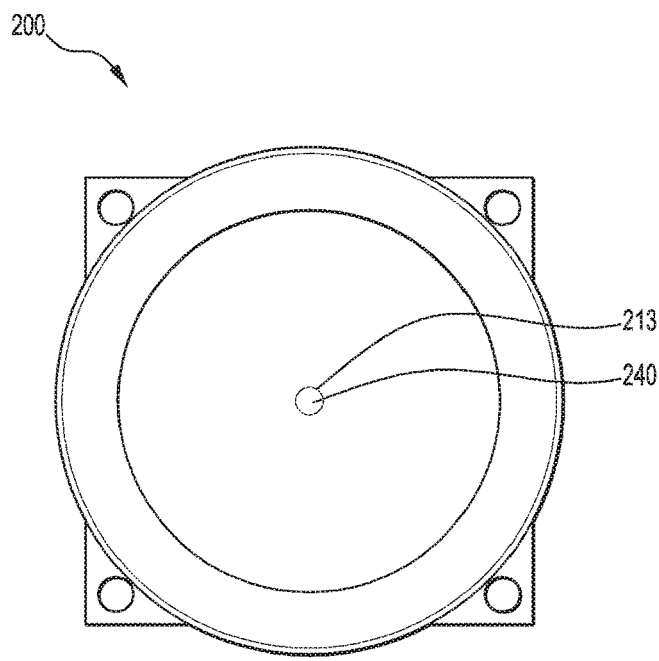
FIG. 7 shows a front view of the photobleaching device shown in FIG. 6.
Figure 8:
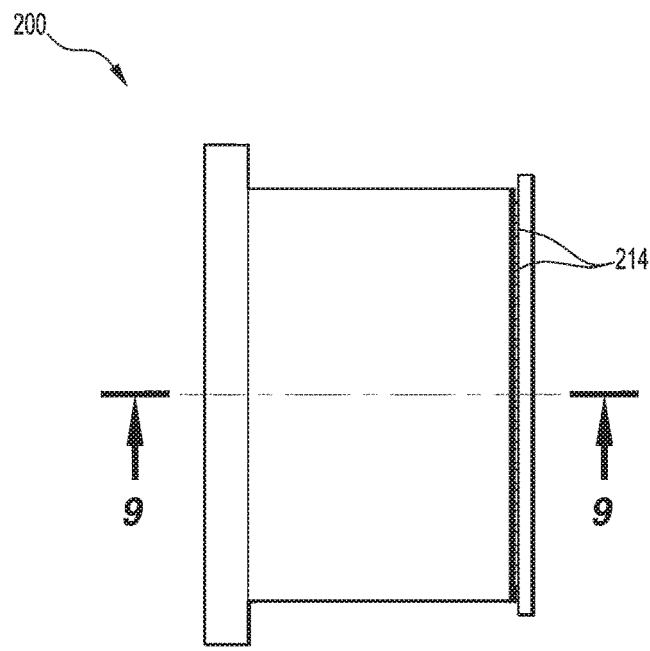
FIG. 8 shows a side view of the photobleaching device shown in FIG. 6.

Light guide 208 comprises a light guide optical medium 210. The light guide optical medium 210 may be comprised of acrylic and may comprise a reflective or a total reflective surface 218 on the parts pf its exterior that do not provide light to eye 198. The light guide 208 is illuminated by light source 206. The light guide 208 embodiment shown in FIGS. 1 to 10 also comprises a concave surface 216. FIGS. 1 and 6 show the concave surface 216 of light guide 208 to comprise facets 217. In the embodiments shown in FIGS. 11 to 14 the concave surface 216 does not comprise facets.

The illumination source 206 in the light guide 208 bleaching embodiments (FIGS. 1 to 10) and light guide 208 bleaching with a curved light source 221 embodiments (FIGS. 11 to 14) comprises an illumination panel 212 comprising a plurality of LEDs 214 disposed on a surface of panel 212. All illustrated embodiments of light guide 208 comprise symmetrical illumination panels 212.

Figure 4:
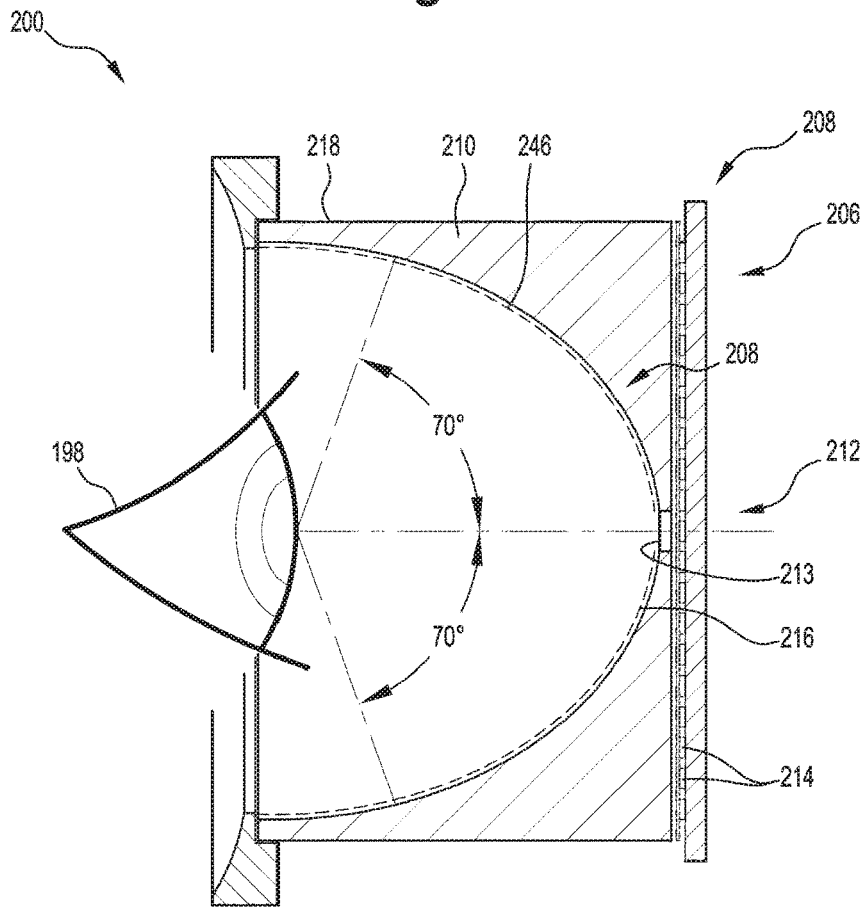
FIG. 4 shows a section view of the photobleaching device shown in FIG. 1, wherein the section is taken along the line indicated by the arrows labelled "4" in FIG. 3.
Figure 5:
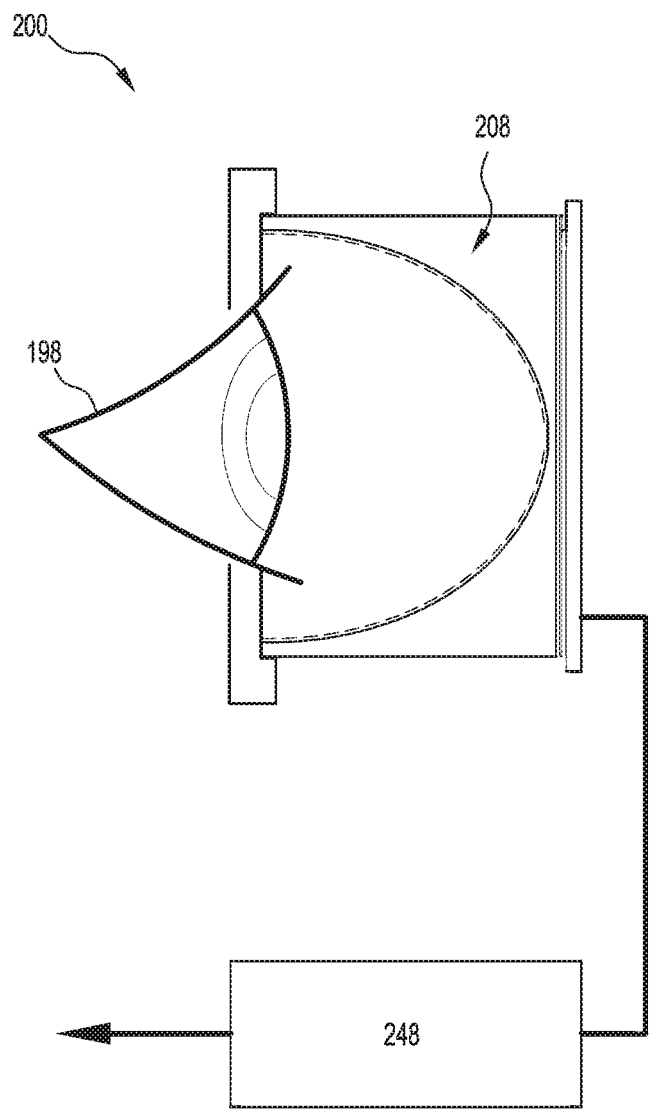
FIG. 5 shows a section view of the photobleaching device shown in FIG. 1 illustrating the positioning of the eye and connection to bleach control device.
Figure 9:
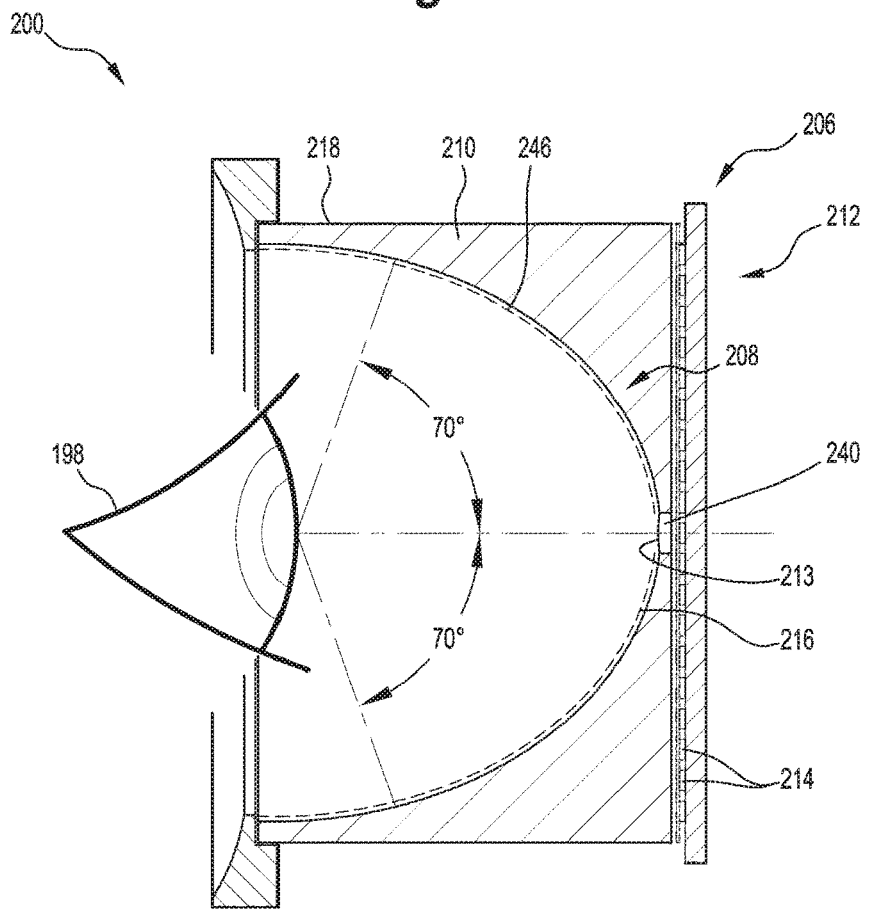
FIG. 9 shows a section view of the photobleaching device shown in FIG. 6, wherein the section is taken along the line indicated by the arrows labelled "9" in FIG. 8.
Figure 10:
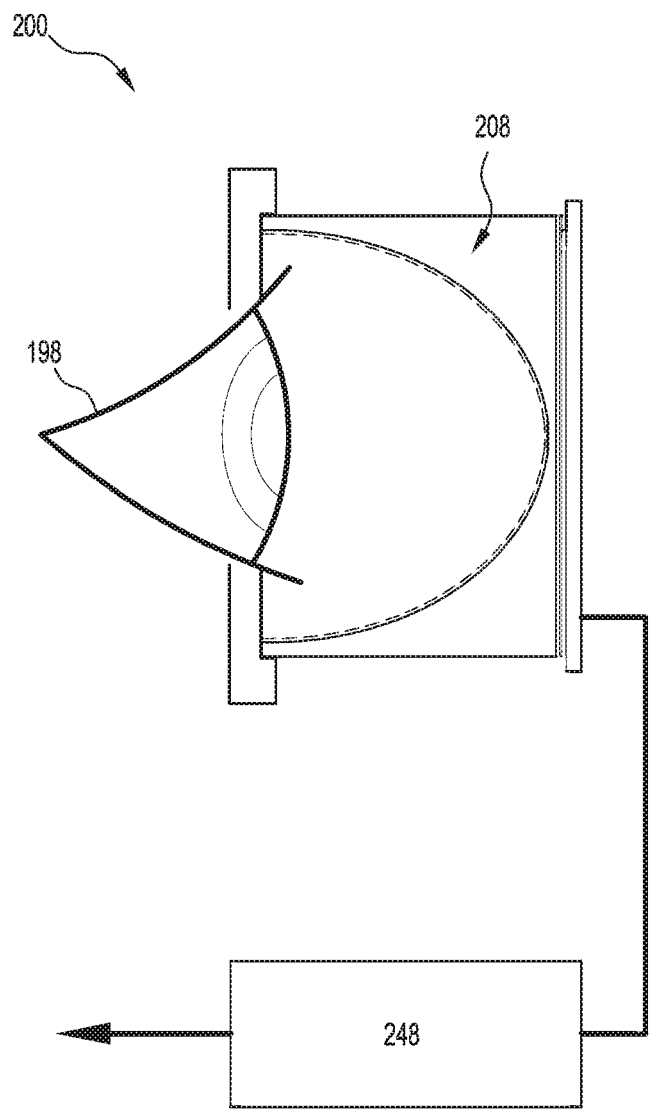
FIG. 10 shows a section view of the photobleaching device shown in FIG. 6, illustrating positioning of the eye and connection to bleach control device.
Figure 11:
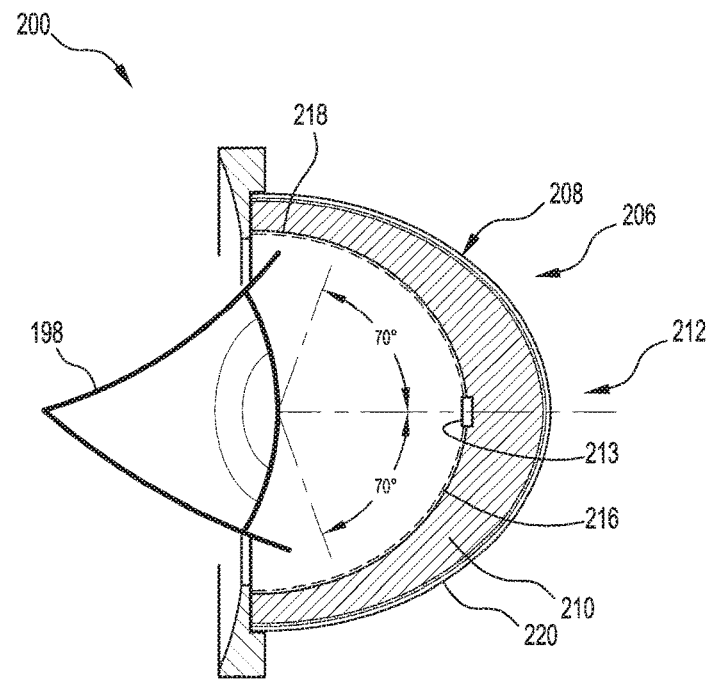
FIG. 11 shows a section view of a photobleaching device according to a second embodiment of the invention comprising a fixation target.
Figure 12:
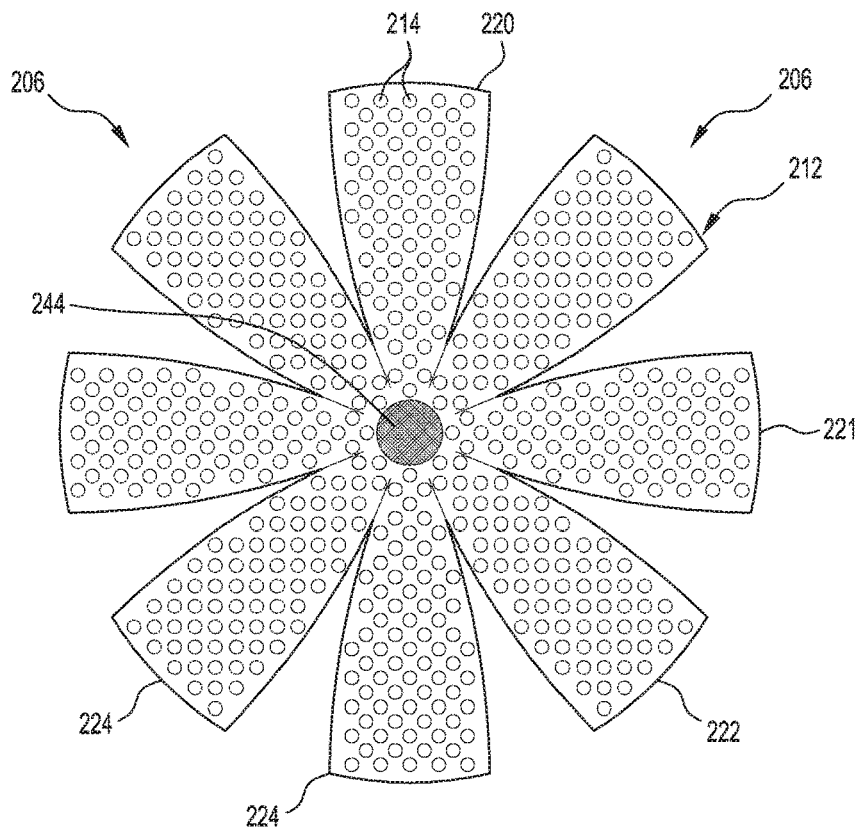
FIG. 12 shows a front view of a curved light source suitable for use in the photobleaching device shown in FIG. 11.
Figure 13:
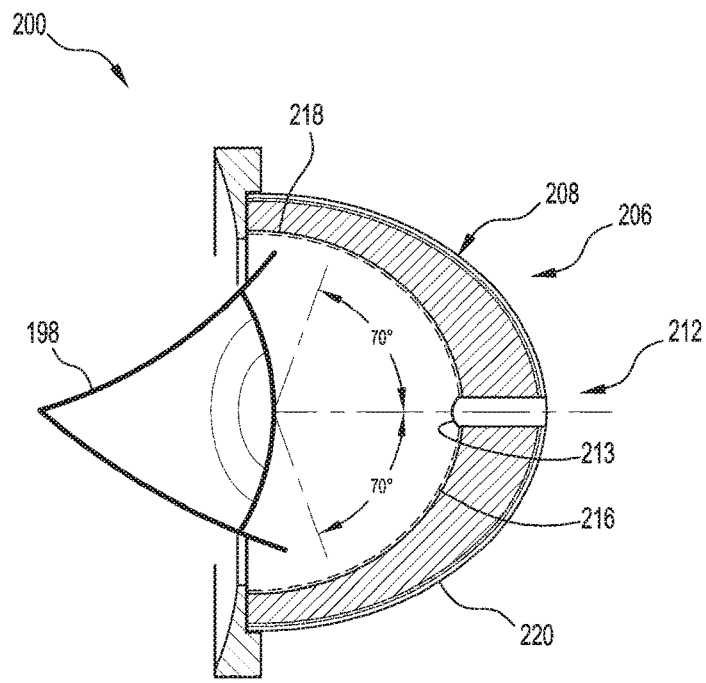
FIG. 13 shows a section view of a photobleaching device according to a second embodiment of the invention comprising an imaging system.

The illumination panels 212 shown in FIGS. 1 to 10 comprise an aperture or orifice 213 for the transmission of light to imaging sensor 240 or fixation target 244. FIGS. 4 and 9 show LEDs 214 to be spaced over substantially the entire surface of planar, circular panel 212. FIGS. 12 and 14 also show LEDs 214 to be spaced over substantially the entire surface of arcuate light source 221. The curved or arcuate light source 221 comprises an unfolded spherical shape 222 comprising a plurality of petals or wings 224. Arcuate light source 221 comprises or is disposed on a flexible printed circuit board (PCB) 220.

As will be readily understood by a skilled person, illumination source 206 may comprise a Köhler illumination source. As used herein "Köhler illumination" is also known for ophthalmic applications as Maxwellian Viewing Systems. The main characteristic of this concept is that an illumination source is imaged onto the pupil plane of the eye. With this, spacial features of the light source are not visible on the retinal plane and highly even illumination is achieved. More sophisticated versions can be derived wherein the apertures at the conjugate planes can control sharp edges of the illuminated field as well as control the brightness.

The embodiments shown in FIGS. 11 to 14 illustrate an embodiment comprising an integrating sphere 230 comprising a white diffuse coating 234, a baffle 236, an entry port 238 and an exit port 239. The illumination source 206 shown in FIG. 2C comprises a xenon flash lamp. In other embodiments, one or more high intensity LED may be used.

An integrating sphere, also known as an Ulbricht sphere, is an optical component consisting of a hollow spherical cavity with its interior covered with a diffuse white reflective coating, with small holes for entrance and exit ports. Its relevant property is a uniform scattering or diffusing effect. Light rays incident on any point on the inner surface are, by multiple scattering reflections, distributed equally to all other points. The effects of the original direction of light are minimized. An integrating sphere may be thought of as a diffuser which preserves power but destroys spatial information.

The device 200 may also comprise a bleach control device 248 to control the brightness and pulse form of the illumination source 206. The brightness and pulse form of the illumination source 206 is controlled with bleach control device 248. The bleach control device 248 may be connected to or comprised within a perimetry device 100 such as dark adapted perimetry device 100 described below. The connection may be to control unit 124. The bleach control device 248 may comprise a printed circuit board.

Bleaching device 200 may also comprise a spectral filter 246 to filter the light incident upon the eye. Although not shown in FIGS. 11 to 14, the integrating sphere 230 may also be used with a spectral filter 246. In the integrating sphere 230 embodiments the spectral filter may be located between eye 198 and sphere 230. In the light guide 208 bleaching embodiments (FIGS. 1 to 10) and light guide 208 bleaching with a curved light source 221 embodiments (FIGS. 11 to 14) the spectral filter 246 may be located between illumination source 206 and a light guide 208 or between a light guide 208 and the eye 198.

The spectral filter 246 should not cover the imaging system 240 or the fixation target 244. The spectral filter 246 may comprise an aperture for the imaging system 240 or the fixation target 244.

In one embodiment, the present invention is distinguished from other retinal bleaching methods by providing a selective and substantially even illumination over a large portion of the retina (Ganzfeld). The present invention may provide selective illumination over an area on the order of 100 degrees field of view or more. This is of significant advantage because it is known that specific spectral exposure for the stimulus is desired to discriminate AMD sensitive test results. This is also true for initial bleaching.

Of significant advantage is that the present invention provides measurements within a field of view comprising a substantial area of the retina with up to 72 deg eccentricity. In another embodiment of the field of view is greater than 40 deg eccentricity. In other embodiments the field of view comprises more than 35; more than 40; more than 50, or more than 70 deg eccentricity.

The present invention may utilise a bleaching level of 30-95%, depending on the application. Once the bleaching has been performed, the bleaching device is removed from the optical path.

In one embodiment, the invention presents a bleaching device 200 that is able to provide substantially even illumination over a large portion of the retina and a known bleaching level. As noted above, bleaching device 200 may be equipped with a spectral filter 246. This can be advantageous for achieving a specific bleaching behaviour to reduce measuring time to the rod cone break. Additionally, a diaphragm (not shown) may be applied to the bleaching device 200 to illuminate desired portions of the retina and correspondingly prevent exposure of other areas on the retina. The diaphragm may comprise an aperture, whose conjugate image on the retina produces a sharp edge of the illuminated area.

The present invention is the first to provide illumination of such large portions of the retina, and the first to do so with a high level of accuracy.

The illumination source 206 may further comprise an image forming system (not shown) disposing radiation of the object plane into the image plane of the bleaching device 200. The aperture size of the imaging forming device may be conjugate to the retinal observable field. The object plane size of the bleaching device 200 is conjugate to the entrance pupil size of eye 198. The bleaching device 200 may further comprise a filter (not shown) placed in the image path of the bleaching device disposing filtered radiation onto the retina.

Dark Adapted Perimetry Device

Conventional displays are constrained to approximately three log units of luminance and are unable to produce very low light levels. The range of cone and rod recovery spans between five to six log units and may be three to four units below the capacity of conventional CRT displays. While this capacity may be lowered using neutral density (ND) filters, visual acuity (VA) remains a poor measurement for detecting AMD. This is because early AMD does not often show functional changes despite structural changes.

According to one embodiment of the invention, stimulus exposure may start shortly after bleaching with bleaching device 200. The stimulus is recorded via acknowledging the signal seen through an input unit 190, preferably a button or switch. The values are recorded and related to a time reference point, which in a preferred embodiment coincides with the bleaching pulse.

The subject's eye 198 may be exposed with a plurality of spatially separated stimulus target light sources 114, with only one stimulus light source 114 illuminated at a time. Known exposure parameters for intensity, spectrum and location relative to a fixation axis which forms the origin of the instrument coordinate system for each stimulus target light source 114 intensity may be used.

One embodiment of a dark adapted perimetry device 100 according to the invention is shown in FIG. 18. The body 102 houses an array guide 110 comprising stimulus target array 112 which is comprised of individual stimulus target light sources 114. In the embodiment shown, the array guide 110 absorbs visual radiation and to do this is black.

Light sources 114 comprise an optical transmissive element with diffusing light propagation properties, and a circular exit diaphragm which forms the stimulus surface. The exit diaphragm disposes the radiation to eye 198.

Device 100 also comprises one or more fixation targets 128 (not shown) which assists with the alignment of subjects visual axis of the subject's observed eye with instrument reference axis. Preferably respective fixation targets 128 are located in the centre of array guide 110 and one each located in the left part and in the right part of array guide 110.

An alignment illumination source 129 is shown on a front surface of body 102. The reflection of alignment illumination source 129 may be used in a captured image of eye 198 to provide information on the alignment of eye 198. In one embodiment illumination source 129 is an infrared illumination source. Alignment illumination source may comprise a ring or point light source.

Further a tracking device 122 is comprised to correlate the activated stimulus target light source 114 to a location on the retina of eye 198 where the measurements of both locations have been acquired at the time of the subject response.

Figure 20:
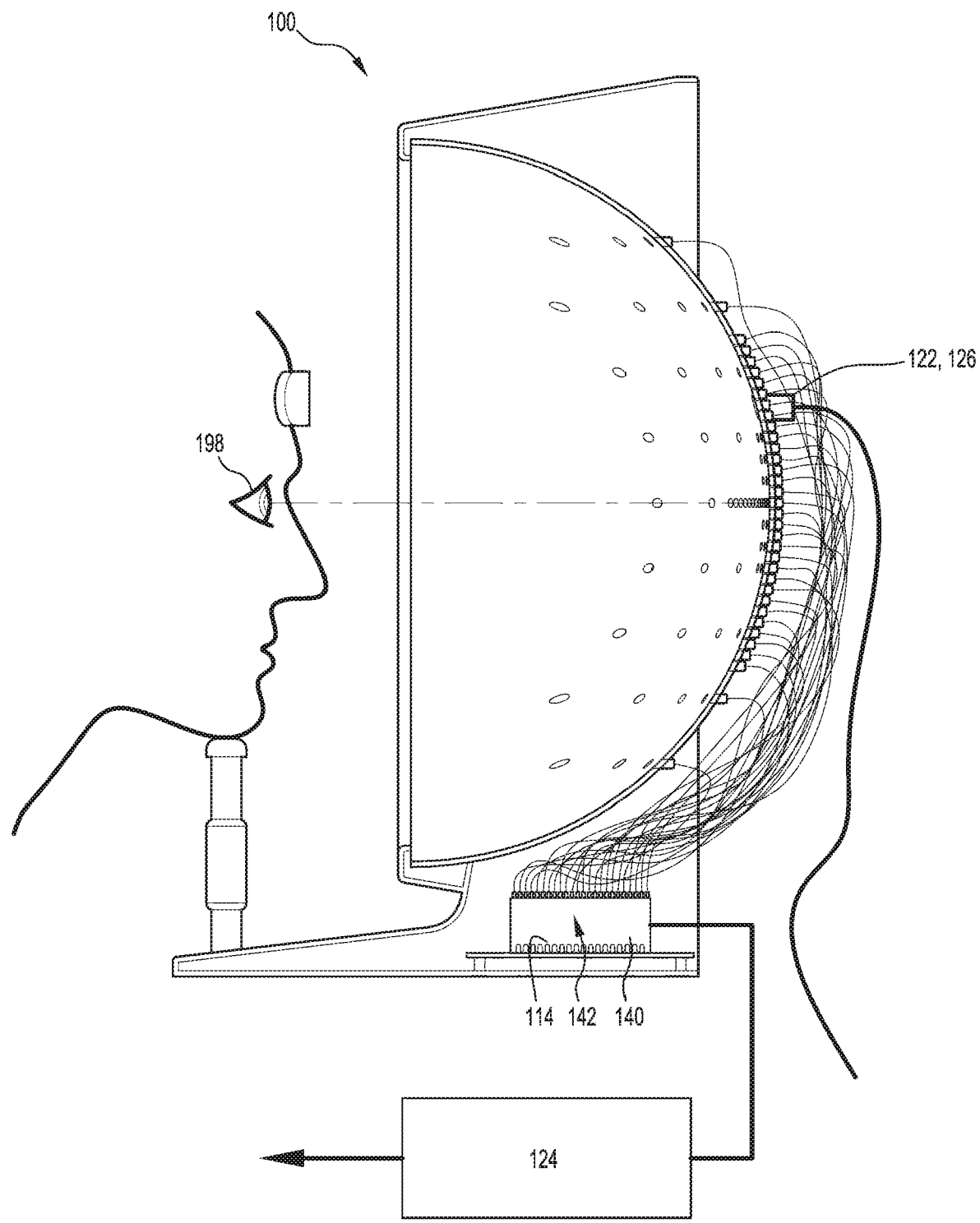
FIG. 20 shows a section view of the dark adapted perimetry device shown in FIG. 18, wherein the section is taken along the line indicated by the arrows labelled "20" in FIG. 19.

A control unit 124 (see FIG. 20) is also comprised to present controlled and selective stimulus target light source 114 illumination at a specific location, record exposure parameters at the time of subject response through the input unit 190, and record the time relative to a time reference point for the measurement. The control unit 124 may comprise a programmable logic controller.

The exposure parameters at subject's response to said exposure of each activated stimulus may be recorded and related in time to a time reference point.

As discussed below, accuracy improvement may be achieved by processing the exposure parameters to reduce measurement uncertainty. The processing may be performed using said recorded exposure parameters with at least two different locations relative to the instrument coordinate system.

The method may further include processing of the accuracy improved data to establish characteristic adaption parameters of eye 198.

A further step in the method may be a comparison of the characteristic adaption parameters of eye 198 with said normative reference.

The captured data can be noisy. In order to provide highly accurate data that can be used for diagnostic purposes, the invention also provides an accuracy improvement method. One shortcoming of prior art methods is that only a single stimulus point is observed over time and then noise reduction is performed along these data points. The present invention correlates the responses of neighbouring stimulus points with the single point data and performs noise reduction thereon. A curve or set of curves may be formed to express the relationship between responses of neighbouring points on the retina. The skilled person will realise that only one point can be obtained at one time and that said response time is used as one of the parameters in said relationship.

From the teaching herein, a skilled person is readily able to select a suitable noise reduction algorithm. While any of the known methods of noise reduction can be applied, suitable ones include least square fitting, generalised cross validation or maximum likelihood estimation. The noise reduction may comprise reduction at a common intensity level or across a surface normal.

In one embodiment, the present invention uses a normative data set that has been statistically derived though clinical trials to establish normal response characteristics of stimuli. The normative data is compared with the noise reduced response data derived from the accuracy improvement methods. Significantly, this comparison may in turn be used in the diagnosis of diseases of the retina and preferably for the diagnosis of early AMD.

The light sources 114 have the capacity to display a spectral distribution with a dominant wavelength that coincides with the peak sensitivity of the rod and the cone receptors (L, M and S receptors). In one embodiment only one wavelength is displayed at a time.

Another embodiment has a spectral distribution of the dominant wavelengths that coincide with the isoluminant responses of two said receptors of the normal scotopic viewer. This has the advantage of detecting receptor differences directly through direct comparison, and produces overall lower noise in the measurements.

The comparison between the normative data and the measurement data may be displayed in a novel method topographically onto the retinal coordinate system displaying derived characteristics with additional numerical, color or graphical means representing a third dimension. The display may be a 3-D visualization by intensity or by response time.

Additionally by overlaying this display, an additional level of detail may be displayed, for example temporal data may be visualized with an overlay.

The complexity of the information of a retinal coordinate system includes information of response sensitivity, response time, rate of change in response sensitivity achieved through determining a derivative of the response function, and other derived characteristics including cone break. These are preferred characteristics, but the invention is not limited to these.

Sudden changes in response from neighbouring points on the retina may also indicate retinal defects. Additionally, characteristics like rod-cone ratio may be derived by applying different spectral stimuli to the same stimulus location, which are substantially coincident in the spectral sensitivity to the receptor sensitivities.

Combining these different stimulus responses gives additional information in regards to rod-cone behaviour and rod-cone density, helping further in the diagnosis of disease. This accuracy of the different spectral responses may be further improved by determining the lens density of the subject's ocular media. The lens density is measured by performing at least three measurement at least three different wavelength. One that is sensitive to scatter (blue); one that is less sensitive to scatter (red); with the third one between these two (yellow or blue (cyan) at the visual axis of the retina.

In other embodiments, the device 100 uses a minimum of two colours or four colours to discriminate lens density. The use of at least three colours is more robust and reliable and provides a common reference to the two. Lens density defects may be detected in different colour shades, depending on the underlying cause, for this possibly the fourth color can be used. A four point ratio will be also more accurate than a two point ratio.

In order to perform accurate correlation of measurements to the actual retinal positions, tracking device 122 is used. The tracking device 122 correlates a characteristic of the eye that is unique relative to the location of the retina. The perimetry device 100 presents an activated stimulus target light source 114 relative to the instrument axis. The tracking device 122 records at least two of these unique characteristics at the time of stimulus response and a control unit 124 correlates these sets of points to determine the location of the retina that was exposed by the stimulus target light source 114.

Three methods are presented to acquire the characteristics of the eye 198. One is to project a pattern of at least three points or a ring pattern onto the cornea or other ocular surfaces and capture the image of this reflection. This first method is well known as purkinje images, where the invention makes use of the brightest purkinje images for analysis of gaze which are the 1st purkinje image which is derived from the anterior corneal surface and the $3^{rd}$ purkinje image, which is derived from the anterior lens surface. Another method is to capture patterns (at least 2 points) on the iris or pupil together with information on the surrounding area of the eye not being part of the eye (at least 2 points). The third method is to illuminate at capture with a retinal imaging device at least one small portion of the retina. The rotation of at least one of the characteristic location points is captured against the fixation axis at the time of response. The difference of the two locations is the measure of deviation from the instrument axis.

Ambient light can contaminate the measurement noticeably, as the measurements are performed at extremely low light levels. Ambient light needs to be eliminated as much as possible. The invention presents a shield 120 (not shown) which provides a means of shielding the measuring system from unintended light by surrounding the functional components with a baffle that is incorporated or attached to the perimetry device 100.

Further a pupil measuring device 126 (FIG. 20) is comprised in perimetry device 100 to capture and measure the size of the pupil at the time of stimulus response by the subject. This value is used to correct the measured response values to retinal exposure levels, commonly known as troland.

As noted above, one or more fixation target 128 is presented at the instrument coordinate origin or at an offset position in the horizontal plane intersecting the origin depending on which portions of the retina are measured, with the visual axis representing one of the coordinate axes. As the bleaching recovery progresses and hence the visual sensitivity increases, the brightness of the fixation target 128 is adjusted as a function of this recovery and changes from initially a bright level to a dimmer level in order to present maintain substantially the same exposure level relative to the expected stimulus target light source 114 level.

The invention may also comprise accuracy improvement wherein the stimulus exposure parameters are processed to reduce measuring uncertainty, the processing may be performed using said recorded exposure parameters with at least two different locations relative to the instrument coordinate system.

The invention may also comprise the processing of accuracy improved data to establish characteristic adaption parameters of said subject's eye.

The invention may further comprise a comparison of said subject's characteristic adaption parameters with said normative reference.

The present invention also provides a method of topographically displaying the comparison of rod and cone characteristics, the method comprising comparing said subject's characteristic adaption parameters; a two dimensional coordinate system and coordinates representing the retinal locations; allocation of adaption parameter values to said retinal coordinates; a color scale where colors are associated to adaption parameters; Representation of the adaption parameters as planar graphical display values with the retinal coordinates in the viewing plane, where these values are displayed with at least one or in combination as said color, as a numerical value, contours of equal value.

The method of topographically displaying the comparison of rod and cone characteristics may further comprise presenting information of more than three dimensions, comprising: a rotated planar topographical display where coordinate origin is not normal to viewing plane, wherein an additional dimension is represented as a coordinate value normal to the retinal coordinates; and the additional dimensional information is represented by displaying a section of the said topographical display simultaneously as a 2D planar display with retinal coordinates as one ordinate, the adaption parameter as a second ordinate, and the additional dimensional information as a colour, numerical or graphical display. The colour, numerical or graphical display may comprise one or more of contours, dots and/or vectors.

In another embodiment, the additional dimensional information may be overlayed with numerical, graphical and color information. The overlay may comprise one or more of black/white weighting of color, coloring of numerical values and contours and vectors. The present invention also provides a method to eliminate the effects of transmissive ocular properties (lens density LD) from the measurement of the stimulus responses. This method comprises the subject fixating at a known stimulus (LD) wherein the LD stimulus emits at least three dominant wavelengths. At least one of these wavelengths is sensitive to scattering properties of the subject's ocular medium. Another of the wavelengths is substantially insensitive to said scattering properties. The stimuli are presented at different times and said exposure is increased from low intensity level that is undetectable by subject until the stimulus is seen. The subject's response to the observed stimulus is then recorded and a determination of transmissive ocular properties is made by combining said recorded LD stimulus measurements. Any transmissive effects may be eliminated by combining this response with the methods described above.

This highlights yet another advantage of the present invention which is the detection of visual thresholds in the order of $10^{-6}$ cd/m$^2$.

The perimetry device 100 may further comprise, a processing unit 130 for performing accuracy improvement of as described herein wherein the stored measurement points are processed into graphical and numerical data outputs and characteristic values, where the outputs include the dark adaptation response of cones and rods.

The device 100 may further comprise a storage unit 132 storing one or more of predetermined normative references, image data, analysis results and characteristic parameters of the stimulus targets.

The perimetry device 100 may further comprise a display unit 134 presenting the outputs of the processing unit 130.

The device may further comprise a fixation structure 136 supporting and stabilising the patient's head and its position relative to the perimetry device reference axis during a test. As shown in FIG. 18, the fixation structure 136 may also provide a base for attachment of locator 204.

In one embodiment, the dominant wavelength of the spectrum of each of the plurality of stimulus target light sources 114 may be selected to coincide with peak responses of the visual receptors in the human eye/retina.

Control Unit and Dynamic Range

The control unit 124 delivers the full dynamic range of stimulus luminance in the order of 75 dB (ratio of >20×106:1) through electronic means. The minimum visual threshold is in the order of 10-6 cd/m2 and requires the novel methods of the control unit 124 to achieve required accuracy and resolution.

In order to achieve the said dynamic range of stimulus luminance, at least two means of modulations are used. The first comprises a pulse width modulation (PWM) of the light intensity signal by varying the on/off period of the stimulus target light source 114.

Figure 21:
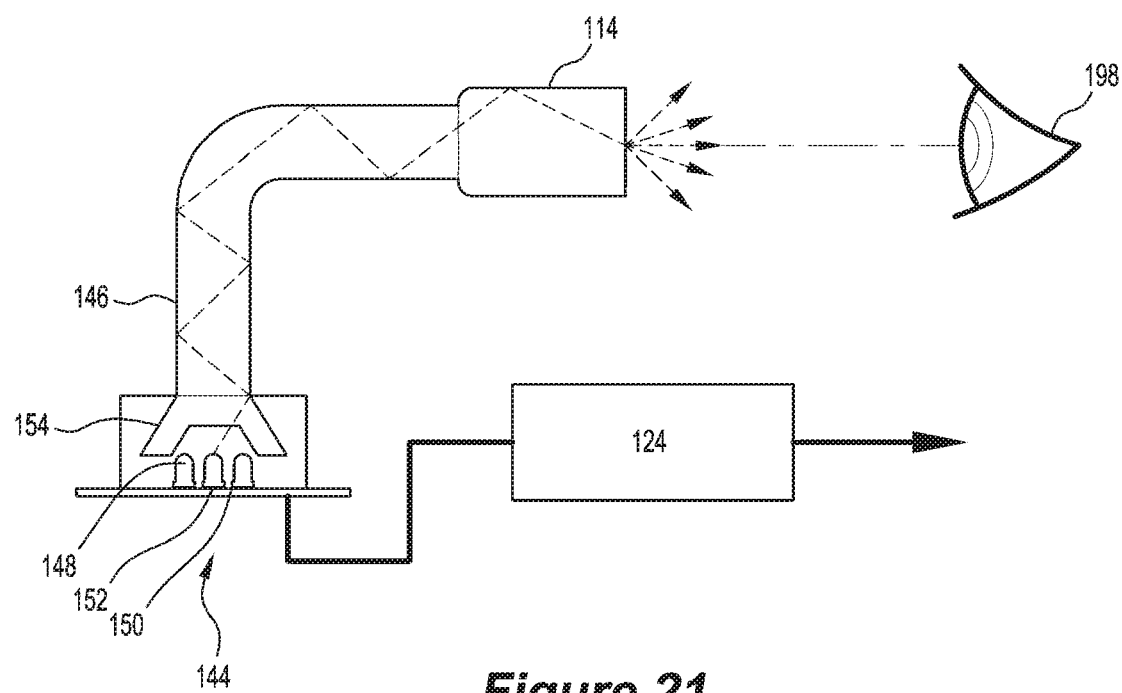
FIG. 21 is a schematic diagram showing one embodiment of an LED complex source.

The second comprises LED current level modulation. In this embodiment, as shown for example in FIG. 21 a light well 140 (see FIGS. 20 and 21) is used. Light well 140 comprises an array of LED sources 142 complementary to the stimulus target array 112. Each LED complex source 144 provides the illumination used to activate a complementary stimulus target light source 114. Each LED complex source 144 is connected to the stimulus target light source 114 through a respective fibre optic cable 146. Each respective optical fibre 146 may be illuminated by a respective light source 144. The respective light source 144 may comprise a LED complex light source. The LED complex light source 144 may illuminate one or more light guide 154 which illuminates the respective optical fibre 146.

In this second method of modulation the on level of the PWM is the LED current of a first LED (LED A) 148 within the LED complex source. The off level LED current of the PWM is at zero in the preferred embodiment, however a LED-LOW current level that is greater than zero and lower than the LED current may be also used.

A third means of modulation is advantageous but not essential to the invention. The third means increases the dynamic range of the stimulus luminance by utilising a second LED (LED B) 150 of the same wavelength to the first LED (LED A) 148 for each stimulus target light source 114. This third means, or dual light source modulation, allows for switching between first LED 148 which comprises a high intensity 148 and second LED 150 which comprises a low intensity LED to produce a light output on the stimulus substantially lower than with the first LED (LED A) 148 alone. The same modulations apply of the first 148 and second LEDs 150 (LEDs A and B).

That is, first LED 148 may comprise a high intensity LED and can be powered to get the brightest light and second LED 150 may comprise a low intensity LED to show the lowest light. As such, by utilizing an LED complex source 144 comprising two or more LED light sources, perimetry device 100 can generate a much larger range of outputs than a single LED. First LED 148 and second LED 150 are never activated at the same time, so there is still always only one LED running.

The wavelength of the high intensity LED and the low intensity LED may comprise red.

The light power range of the high intensity LED 148 and the low intensity LED 150 may overlap, however the maximum intensity of the high intensity LED 148 is higher than the maximum intensity of the low intensity LED 150. The maximum intensity of the high intensity LED 148 may be 25 dB higher than the low intensity LED 150.

In another embodiment the LED complex source 144 may further comprise a LED of a second wavelength 152. The second wavelength LED 152 may comprise green.

Figure 22:
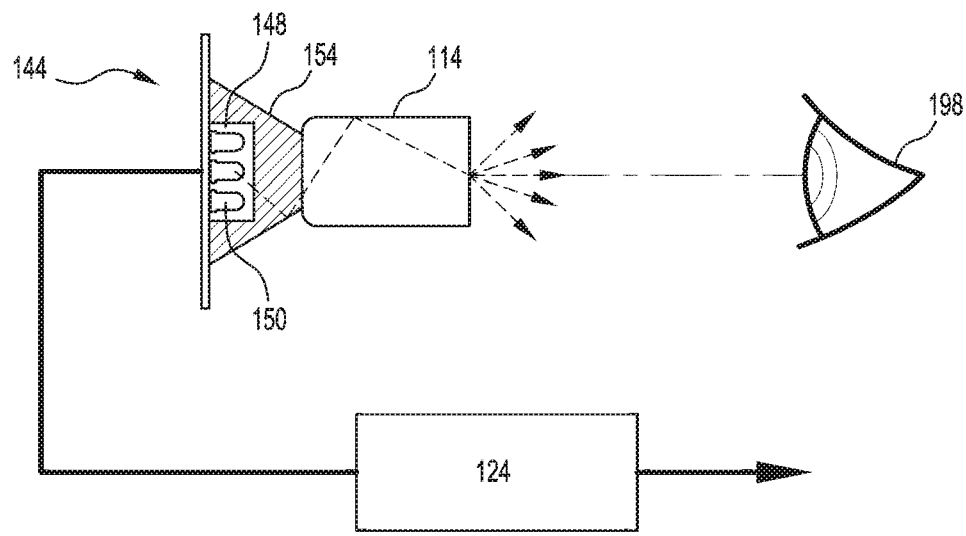
FIG. 22 is a schematic diagram showing another embodiment of an LED complex source.

FIG. 22 shows another embodiment which does not use fibre optic cables 146. Instead LED complex source 144 illuminates one or more light guide 154 which illuminates a respective stimulus target light source 114.

The control unit 124 may apply the stored characteristics of the stimulus target light source 114 to control said luminance at the required magnitude and precision into the said modulations and corresponding magnitudes.

Another significant advantage of the present invention is that the dynamic range of measurement with this invention has been largely increased to about 75 dB dynamic range. In another embodiment, the dynamic range of measurement is about 75 dB. In other embodiments, the dynamic range may be about 50 dB; about 60 dB; about 70 dB; about 80 db; about 90 dB; or about 100 dB.

Fixation Target

A fixation target 128 of the perimetry device 100, where the intensity of the fixation target 128 may be controlled by the control unit 124 and may be changed with the bleaching recovery of the subject. The preferred method maintains a luminance ratio between the target illumination and the expected luminance response at the line of sight level of the subject at the point of time during the test. The preferred method may use a range of discrete brightness levels corresponding to the levels of recovery.

Processing Unit

The device may comprise a processing unit 130 that cross correlates neighbouring stimulus signals. The prior art apparatus and method measure the temporal rod-cone recovery of only a single stimulus. The present invention may consider at least two neighbouring stimuli points. Each stimulus may be characterised with a different temporal rod-cone recovery curve, as the rod cone density changes with eccentricity from the fovea. Each stimulus response may be correlated to the neighbouring stimulus response(s) with a weighting function that is dependent on the distance between the points and the statistical confidence of the data points. The preferred embodiments include a plurality of stimuli points. This may be performed as a series of lines or curves along the retinal coordinates, or as a topographical correlation between points of retinal coordinates.

To further improve the parameters of temporal rod cone response graph (reduction of least square deviation), known statistical methods for curve fitting methods may be applied. These include but are not limited to the below mentioned methods like MLE (maximum likelihood estimator), GCV (generalised cross validation), least squares, moving averaging, (note, the mathematical dimension of rod-cone response model is two for the temporal rod cone response and increased by one for a line scan or two for an aerial scan for the retinal coordinates and curves may be presented as clusters of lower orders). The systematic uncertainties and accuracy is further improved as the increased number of measuring points (cross correlated stimuli points) help reducing measuring uncertainty. Further, the said responses of neighbouring stimuli target light sources 114 are subtracted or as preferred embodiment a partial derivate to each of the said dimensions formed. Characteristics of portions of the derivative space are used to describe physiological properties and diseases of the eye 198.

Such physiological properties include rod-cone ratio for each stimulus target light source 114 location in particular when the stimulus target light source 114 are exposed to at least two dominant wavelengths that are largely different to the exposed rod or cones respectively. Correlation of the multispectral stimulus responses with the rod cone ratio in the processing unit 130 is used as means for the said disease detection.

Shield—Shielding of Ambient Light

The perimetry device 100 may also include a shield 120 (not shown) comprising an occluding barrier that partly surrounds the perimetry device 100. The shield 120 acts to prevent external light stimulating the test subject.

In one embodiment the shield 120 is opaque in the visible electromagnetic spectrum, and comprises an absorbing surface and a diffusing surface so no direct radiation from an undesired ambient light source and no reflections from a stimulus point or any other ambient radiation can be detected by the subject.

The shield 120 may be comprised as an integral component of the device 100 or may be removably attached to device 100.

The skilled person readily understands that the shield 120 should be positioned to surround a substantial portion of the array guide 110 and to enclose the direct light paths between all stimulus target light sources 114 and the test subject's eye.

Tracking Device

A tracking device 122 of the perimetry device 100 comprises a fixation target 128 as described above; an amplitude beam splitter diaphragm 160 (not shown), with an aperture 162 (not shown) covering the whole field of view for the stimulus target light sources 114; a collimating mirror 170 (not shown); an imaging objective lens system 172 (not shown); and an imaging camera 174 (not shown), viewing a portion of the retina. The skilled person readily understands that the fixation target 128 should be positioned so that the gaze of the subject's eye is directed toward the centre of said fixation target 128.

In another embodiment the tracking device 122 comprises a fixation target 128 as described above as well as a light pattern disposing infrared illumination onto the cornea of the test subject. The light pattern may be distributed substantially symmetrically around the test pattern. The light pattern may comprise at least one light point or thin circular section for each direct horizontally and vertically. The circular section may extend to a closed circular ring wherein the illuminated circular section or ring is located outside the said stimulus target array 112. A camera 178 (not shown) with an imaging lens 180 (not shown) may be located in the centre of the stimulus target array 112 forming an image of the reflected light pattern off the subject's cornea and the fixation target 128.

Tracking device processing unit 176 (not shown) may calculate the location and rotational coordinates of the subject's eye from the said image of the light pattern. The tracking device processing unit 176 uses image information of said camera 178 with orientation of the gaze of the subject's eye 198 (e.g. reference to known stimulus points) at known positions in space of the reference point of the subject's eye 198. With the known location of the eye relative to the instrument axis and the known gaze, all information of the spatial location of the eye 198 and rotational state relative to the instrument coordinate system is sufficiently defined. Commonly known geometric rules may be used to calculate through said algorithm these parameters and establish registration of the retinal coordinates to the instrument coordinates.

A third type of tracking device 122 may also be used with perimetry device 100. This third type comprises a fixation target 128 as described above and a camera 178 with an imaging lens 180 with its entrance pupil located in proximity of the stimulus target array 112 The camera 178 is used to detect at least one detectable feature near the subject's eye pupil plane (EPP) of the examined eye 198, features like the iris or pupil and at least two features on the subject's head and an illumination emitting infrared radiation towards the EPP and features on the head.

The camera 178 is used to obtain an image of the EPP and features taken at the time of stimulus response. A tracking device processing unit 176 is used to determine the rotational coordinates from the said image of the subject's EPP and features on the head and establish registration of the stimulus coordinates to the rotation coordinates relative to said reference axis.

At least one image of the EPP and features on the head taken at a known rotational coordinates as the fixation axis, which is used to determine physiological rotational parameters of the eye.

Pupil Measuring Device

Device 100 may also comprise a pupil measuring device 182 (not shown) to record the subject's pupil size. The pupil measuring device 182 may conveniently comprise the imaging camera 178.

Of significant advantage, the recorded rod-cone response value may be corrected with the measure pupil size at the time of patient response to the corresponding stimulus luminance with said processing unit 130 to provide means for expressing rod-cone response as the portion of stimulus radiation disposed on the retina.

Lens Density

Device 100 may also comprise a means for determining the lens density of the ocular lens of the test subject's ocular media comprising at least one stimulus disposing radiation of at least three different dominant wavelengths.

Preferably, only one dominant wavelength is presented at a time and the difference in response to the different dominant wavelengths is used in the processing unit to determine the lens density parameters.

The present invention provides a high quality, highly specific solution to the issue of measuring rod recovery.

In this specification, the terms "comprises", "comprising" or similar terms are intended to mean a non-exclusive inclusion, such that an apparatus that comprises a list of elements does not include those elements solely, but may well include other elements not listed.

Throughout the specification the aim has been to describe the invention without limiting the invention to any one embodiment or specific collection of features. Persons skilled in the relevant art may realize variations from the specific embodiments that will nonetheless fall within the scope of the invention.

The claims defining the invention are as follows:

1. A dark adapted perimetry device comprising:
   a photobleaching device;
   a concave array guide, the array guide comprising a stimulus target array comprising a plurality of stimulus target light sources positioned within the array guide, wherein each stimulus target light source is illuminated by a respective LED complex light source, wherein each respective LED complex light source comprises a high intensity LED and a low intensity LED of a same wavelength, the high intensity LED having a maximum intensity greater than a maximum intensity of the low intensity LED; and
   a control unit to selectively illuminate light sources comprised in the plurality of stimulus target light sources at a predetermined luminance.

2. The device of claim 1, wherein the control unit is configured to illuminate only one light source at a time and to illuminate each light source each time with known exposure parameters for one or more of intensity, spectrum, and location relative to a fixation axis.

3. The device of claim 1, wherein each stimulus target light source comprises an optically transmissive element with diffusing light propagation properties, and a circular exit diaphragm which forms a stimulus surface.

4. The device of claim 1, wherein each stimulus target light source is connected to a respective optical fibre.

5. The device of claim 1, wherein each respective optical fibre is configured to be illuminated by a respective light source.

6. The device of claim 1, wherein the control unit is configured to modulate a luminance of each stimulus target light source using one or more of pulse width modulation (PWM), LED current level modulation, and multi-source modulation of the light source.

7. The device of claim 1, wherein the photobleaching device comprises:
   an eye piece for positioning the eye;
   a locator for moving the bleaching device into and out of the optical path;
   an imaging system for tracking the gaze direction or a fixation target;

an illumination source having a brightness; and a bleach control device to control the brightness and a pulse form of the illumination source.

8. The device of claim 7, wherein the illumination source comprises a light guide comprising a light guide optical medium and an illumination panel.

9. The device of claim 7, wherein the illumination source comprises an integrating sphere.

10. The device of claim 7, wherein the bleach control device comprises a spectral filter to filter the light incident upon the eye.

\* \* \* \* \*